United States Patent [19]
Routh

[11] Patent Number: 6,096,064
[45] Date of Patent: *Aug. 1, 2000

[54] FOUR CHAMBER PACER FOR DILATED CARDIOMYOPTHY

[75] Inventor: Andre G. Routh, Lake Jackson, Tex.

[73] Assignee: Intermedics Inc., Angleton, Tex.

[ * ] Notice: This patent issued on a continued prosecution application filed under 37 CFR 1.53(d), and is subject to the twenty year patent term provisions of 35 U.S.C. 154(a)(2).

[21] Appl. No.: 08/933,581

[22] Filed: Sep. 19, 1997

[51] Int. Cl.$^7$ .............................. A61N 1/05; A61N 1/362
[52] U.S. Cl. ................................................................ 607/9
[58] Field of Search .............................. 607/9, 122, 123, 607/125, 126; 600/373–375, 387

[56] References Cited

U.S. PATENT DOCUMENTS

| | | | |
|---|---|---|---|
| 4,444,195 | 4/1984 | Gold | 128/642 |
| 4,708,145 | 11/1987 | Tacker, Jr. et al. | 128/419 |
| 4,727,877 | 3/1988 | Kallok | 128/419 |
| 4,962,767 | 10/1990 | Brownlee | 128/786 |
| 5,099,838 | 3/1992 | Bardy | 128/419 |
| 5,111,811 | 5/1992 | Smits | 128/419 |
| 5,127,403 | 7/1992 | Brownlee | 128/419 |
| 5,314,430 | 5/1994 | Bardy | 607/5 |
| 5,423,772 | 6/1995 | Lurie et al. | 604/282 |
| 5,628,778 | 5/1997 | Kruse et al. | 607/123 |
| 5,720,768 | 2/1998 | Verboven-Nelissen | 607/9 |
| 5,800,465 | 9/1998 | Thompson et al. | 607/9 |

OTHER PUBLICATIONS

Coronary Sinus Atrial Pacing: Radiographic Considerqations; M.J. Hewitt, et al.; American Roentgen Ray Society; Feb. 1981; (pp. 323–328).

Modern Cardiac Pacing, S.S. Barold; Futura Publishing Company, Mount Kisco, NY 1985; (8p.).

Four Chamber Pacing in Dilated Cardiomyopathy; S. Cazeau, et al; PACE, vol. 17, Nov. 1994; (6 p.).

Abstract, "Preliminary Experience with a New Coronary Sinus Lead . . . " Claude Daubert, et al., Cardiostim 275, 1994.

Abstract, "A New Dual Chamber Single Lead System", J. Hirshberg, et al. Cardiostim #273, 1994.

*Primary Examiner*—Jeffrey R. Jastrzab
*Attorney, Agent, or Firm*—Schwegman, Lundberg, Woessner & Kluth, P.A.

[57] ABSTRACT

An endocardial apparatus for pacing four chambers of a heart, comprising: a power source housed in an implantable can, first, second and third leads having proximal and distal ends, each lead being electrically connected to the power source at its proximal end and extending into a vein proximal the heart, the first lead connecting at its distal end to an electrode that is in electrical contact with the right atrium of the heart, the second lead connecting at its distal end to an electrode that is in electrical contact with the right ventricle of the heart, the third lead connecting at a point proximal its distal end to a first electrode that is in electrical contact with the inside of the coronary sinus and oriented so as to stimulate the left atrium of the heart and connecting at its distal end to a second electrode that is in electrical contact with the inside of the great cardiac vein and oriented so as to stimulate the left ventricle of the heart. Devices are also disclosed for orienting and maintaining the position of the electrodes on the third lead.

16 Claims, 5 Drawing Sheets

FOUR CHAMBER PACER FOR DILATED CARDIOMYOPTHY

BACKGROUND OF THE INVENTION

1. Field of the Invention

The present invention relates generally to cardiac stimulating devices, such as pacemakers and defibrillators. More particularly, the present invention relates to a cardiac stimulating device that is capable of pacing all four chambers of the heart without requiring an epicardial lead. Still more particularly, the present invention relates to a pacer that includes pacing electrodes in each of the right atrium and right ventricle and in the coronary sinus/great cardiac vein for pacing the left atrium and left ventricle.

2. Description of the Related Art

In the normal human heart, illustrated in FIG. 1, the sinus (or sinoatrial (SA)) node, generally located near the junction of the superior vena cava and the right atrium, constitutes the primary natural pacemaker by which rhythmic electrical excitation is developed. The cardiac impulse arising from the sinus node is transmitted to the two atrial chambers (or atria) at the right and left sides of the heart. In response to this excitation, the atria contract, pumping blood from those chambers into the respective ventricular chambers (or ventricles). The impulse is transmitted to the ventricles through the atrioventricular (AV) node, and via a conduction system comprising the bundle of His, or common bundle, the right and left bundle branches, and the Purkinje fibers. The transmitted impulse causes the ventricles to contract, the right ventricle pumping unoxygenated blood through the pulmonary artery to the lungs, and the left ventricle pumping oxygenated (arterial) blood through the aorta and the lesser arteries to the body. The right atrium receives the unoxygenated (venous) blood. The blood oxygenated by the lungs is carried via the pulmonary veins to the left atrium.

This action is repeated in a rhythmic cardiac cycle in which the atrial and ventricular chambers alternately contract and pump, then relax and fill. Four one-way valves, between the atrial and ventricular chambers in the right and left sides of the heart (the tricuspid valve and the mitral valve, respectively), and at the exits of the right and left ventricles (the pulmonic and aortic valves, respectively, not shown) prevent backflow or regurgitation of the blood as it moves through the heart and the circulatory system.

The sinus node is spontaneously rhythmic, and the cardiac rhythm originating from the primary natural pacemaker is termed sinus rhythm. This capacity to produce spontaneous cardiac impulses is called rhythmicity, or automaticity. Some other cardiac tissues possess this electrophysiologic property and hence constitute secondary natural pacemakers, but the sinus node is the primary natural pacemaker because it has the fastest spontaneous rate. The secondary natural pacemakers tend to be inhibited by the more rapid rate at which impulses are generated by the sinus node.

The resting rates at which sinus rhythm occurs in normal persons differ between age groups, generally ranging between 110 and 150 beats per minute ("bpm") at birth, and gradually slowing to the range between 65 and 85 bpm usually found in adults. The resting sinus rate (hereinafter termed simply the "sinus rate") varies from one person to another, and despite the aforementioned usual adult range, is generally considered to lie anywhere between 60 and 100 bpm (the "sinus rate range") for the adult population.

Disruption of the natural pacing system as a result of aging or disease is commonly treated by artificial cardiac pacing, by which rhythmic electrical discharges are applied to the heart at a desired rate from an implanted artificial pacemaker. An artificial pacemaker (or "pacer" as it is commonly labeled) is an implantable medical device which delivers electrical pulses to an electrode that is implanted adjacent or into the patient's heart in order to stimulate the heart so that it will beat at a desired rate. If the body's natural pacemaker performs correctly, blood is oxygenated in the lungs and efficiently pumped by the heart to the body's oxygen-demanding tissues. However, when the body's natural pacemaker malfunctions, an implantable pacemaker often is required to properly stimulate the heart. An in-depth explanation of certain cardiac physiology and pacemaker theory of operation is provided in U.S. Pat. No. 4,830,006.

Dilated cardiomyopathy is one type of malfunction of the heart. In dilated cardiomyopathy (DCM), the left, and sometimes also the right, ventricle balloons outward, increasing the diastolic (filled) volume from about 90 cc to about 260 cc. The ventricle wall is stretched thin and the force of contraction of the ventricle is greatly diminished. As a result, the ventricle empties inefficiently and incompletely. In addition, distortion of the ventricle causes distortion of the heart valves in turn, with the result that the valves do not close properly and pumping is less efficient. Because the left side of the heart does not pump effectively, backup of blood in the lungs occurs, causing pulmonary congestion and breathlessness. Additionally, if the right heart is affected, blood can back up in the legs, causing edema. In cases of severe DCM, death is either by pulmonary problems (infection secondary to congestion) or by sudden cardiac death (caused by ventricular fibrillation or electromechanical dissociation). DCM is divided into two main categories. Ischemic cardiomyopathy results when the heart muscle is deprived of oxygen, while when no obvious cause can be found it is called idiopathic cardiomyopathy. DCM is easily detectable using current diagnostic technology.

It is believed that pacing the left side of the heart, and in particular the left ventricle can improve circulation. More specifically, the left ventricle can be paced simultaneously with atrial pacing or shortly after a sensed atrial event, so that the ventricle contracts as blood flows into it from the left atrium. This accelerated ventricular pacing reduces regurgitation through the mitral valve, increases forward blood flow and helps prevent the left ventricle from overfilling.

Referring now to FIG. 2, which shows block diagram of a conventional dual-chamber pulse generator, a battery 11 supplies power for the pacer circuitry which is under the control of a microprocessor 12, which includes logic and memory. The atrial chamber is sensed with a sense amplifier 13 and paced with an output circuit 14. The ventricular chamber is sensed with a second sense amplifier 15 and paced with an output circuit 16. Bidirectional communication with an external programmer is accomplished with a telemetry circuit 17 and antenna. The lower rate behavior of the pacer is controlled by an accelerator 18, which measures exercise activity levels.

Referring now to FIG. 3, and by way of example only, two leads 20, 21 are shown connecting a conventional dual chamber pacemaker 22, such as that described in the preceding paragraph, to a heart. In a conventional dual chamber arrangement, leads 20, 21 are inserted in the right atrium and right ventricle, respectively. Each lead 20, 21 includes at least one stimulating electrode(s) for delivery of electrical impulses to excitable myocardial tissue in the appropriate chamber(s) inside the right side of the patient's heart. As shown in FIG. 3, each lead 20, 21 can include two electrodes, for example tip electrode 23 and ring electrode 24 on lead 20 and tip electrode 25 and ring electrode 26 on lead 21, to provide a total of four electrodes in the heart.

Two-, three-, and four-terminal devices all have been used or suggested as possible electrode schemes. Those skilled in the art will recognize that the pacing apparatus described herein is representative of a variety of devices. The present disclosure is provided merely to establish a context for the description of the invention below and is not intended to limit the scope of the invention in any way.

Pacers today are typically designed to operate in the "inhibited" mode. Inhibited mode pacemakers are also termed "demand" type pacemakers, because a pacing pulse is only generated when needed by the heart. Typically, demand pacemakers sense the patient's natural heart rate and apply stimuli only during periods when the heart rate falls below the desired pacing rate. In a demand pacer electrodes in the leads 20, 21 sense the occurrence of an intrinsic event and transmit this to the microprocessor 12 (FIG. 2) via the sense amplifiers 13 and 15. In addition, many pacers have the ability to sense metabolic demand and to modulate their pacing rate in response to sensed changes in metabolic demand. Pacemakers range from the simple fixed rate, single chamber device that provides demand pacing to highly complex models that provide fully automatic dual chamber pacing and sensing functions. The latter type of pacemaker is the latest in a progression toward physiologic pacing, that is, the mode of artificial pacing that most closely simulates natural pacing.

Because of the number of options available in pacer design, a convention has been established whereby specific pacer configurations are identified according to a code comprising three, four or five letters. The fifth code position describes the antitachycardia functions, if any. Because this position is not applicable to most commonly used pacemaker types, most common codes comprise either three or four letters. For this reason and for simplicity's sake, the fifth code position is omitted from the following table. Each code can be interpreted as follows:

| Code position | 1 | 2 | 3 | 4 |
| --- | --- | --- | --- | --- |
| Function Identified | chamber paced | chamber sensed | response to sensing | programmability, rate modulation |
| Options Available | 0-none A-atrium V-ventricle D-dual (A + V) | 0-none A-atrium V-ventricle D-dual (A + V) | 0-none T-triggered I-inhibited D-dual (T + 1) | 0-none P-programmable M-multi-programmable C-communicating R-rate modulating |

For example, a DDD pacer paces and senses in both the ventricle and atrium and uses a dual type response. If atrial electrical activity is detected before the end of the atrial escape interval, atrial pacing is inhibited and a "sensed" atrio-ventricular (AV) delay is started. Otherwise, an atrial pacing pulse is issued and a "paced" AV delay is initiated. If ventricular electrical activity is sensed before the end of the AV delay, the ventricular pacing output is inhibited, otherwise a ventricular pacing pulse is delivered. Similarly, a WIR pacer paces and senses in the ventricle, uses an inhibited type response and is capable of modulating its rate activity in response to metabolic demand. Of the many possible pacer configurations, four or five are most commonly used. These are WI, WIR, DVI, DDD and DDDR.

Because access to the heart is usually made through the venous system, and more specifically through the superior vena cava, which empties into the right atrium, pacing leads are typically implanted in the right side of the heart. Access to the right ventricle is through the right atrium and tricuspid valve. In most cases, pacing of either the right atrium or the right ventricle will result in a corresponding stimulation of the left atrium or left ventricle respectively, after conduction delays that may not be physiologically and hemodynamically optimal. Thus, when it is desired to independently pace the left ventricle and/or atrium, as in the case of DCM, an alternative system is required.

Referring now to FIG. 4, pacing of the left atrium is often accomplished by providing bifurcating lead adapters 30 and 31, which each split a bipolar connection at the pacer header to form two unipolar leads. Alternatively, the pulse generator connector could be fitted with more receptacles which would accept the additional leads directly without the need for adapters such as 30, 31. This makes available third and fourth leads 35, 32. The third lead 35 is inserted through the ostium 36 of the coronary sinus 37 and positioned so that it is in contact with the wall of the coronary sinus adjacent the left atrium. Thus, three-chamber pacing/sensing can be achieved using three endocardial leads, leaving only the left ventricle un-paced.

Heretofore, independent pacing of the left ventricle has required placement of the fourth lead 32 as an epicardial lead, as there is no practical way to place an endocardial lead on the left side of the heart. Placement of a lead directly in the left ventricular chamber is associated with unacceptable risk of thromboembolism (blood clot) that could lodge in the brain, causing stroke, or in the arteries of the legs, which could lead to gangrene and amputation of the affected limb(s). Epicardial lead 32 contacts the outside, rather than the inside, of the heart, and therefore requires open chest surgery.

Because it is generally desirable to minimize the invasiveness of implantation procedures, there is a need for a pacing system for the left side of the heart that can be completely implanted intravenously and does not require open chest surgery.

SUMMARY OF THE INVENTION

Accordingly, there is herein provided a single-pass endocardial lead that is capable of both sensing and pacing in the left atrium and in the left ventricle. The great cardiac vein (GCV) runs up the anterior aspect of the interventricular (IV) septum and then turns to run along the coronary sinus (CS) between the left atrium and the left ventricle. The GCV becomes the coronary sinus after it is joined by the left posterior ventricular vein. The middle cardiac vein, which runs up the posterior aspect of the IV septum, and the small cardiac vein from the right heart merge and flow into the CS near the point at which the CS empties into the right atrium, the ostium (OS) of the CS. The present invention entails locating leads through the OS of the CS so as to pace and sense the left atrium with electrodes in the CS and pace and sense the left ventricle with electrodes in the GCV or one of its left lateral tributaries, such as the posterior vein.

The present lead comprises a proximal connector that makes electrical contact with an implanted stimulating device and a lead body that includes first electrode(s) that are positioned in the coronary sinus so as to stimulate the left atrium and second electrode(s) positioned in the great cardiac vein or one of its lateral tributaries so as to stimulate the left ventricle.

The present invention can be used in a four-chamber, intravenous pacing system that allows maximum flexibility in pacing. According to one embodiment, a pacing lead is inserted into the ostium of the coronary sinus from the right atrium and paces the left atrium and ventricle using ring and tip electrodes, respectively, a second lead paces the right atrium and a third lead paces the right ventricle. The leads used in the present invention can be unipolar or bipolar, or a combination of these.

In order to ensure good electrical contact and distinct pacing of both the left atrium and left ventricle from the lead positioned in the coronary sinus, the present invention further includes an eccentric stabilizer that biases the ring electrode toward the left atrium. In addition, the tip electrode is positioned beyond the point where the great cardiac vein turns downward toward the base of the heart and includes a second stabilizer that maintains the tip electrode in electrical contact with the left ventricle.

According to a preferred embodiment, each of the stabilizers is constructed of a flexible, electrically insulating, biocompatible material that is sufficiently rigid to support an electrode in a desired position within the coronary sinus. The stabilizer can take the form of a sleeve that surrounds the lead and includes a window or opening through which the electrode is exposed. The sleeve is bowed so that it tends to press the window and exposed electrode against one side of the inside surface of the coronary sinus. By orienting the lead and attached sleeve radially, the desired electrode-sinus contact can be made.

The stabilizer on the tip electrode not only biases the electrode toward one side of the great vein, but also includes tines that engage the inside wall of great vein and thus prevent rotation or displacement of either the tip electrode or the ring electrode in the coronary sinus.

BRIEF DESCRIPTION OF THE DRAWINGS

Other objects and advantages of the invention will become apparent upon reading the following detailed description and upon reference to the accompany drawings, wherein.

DETAILED DESCRIPTION OF A PREFERRED EMBODIMENT

Figure 1:
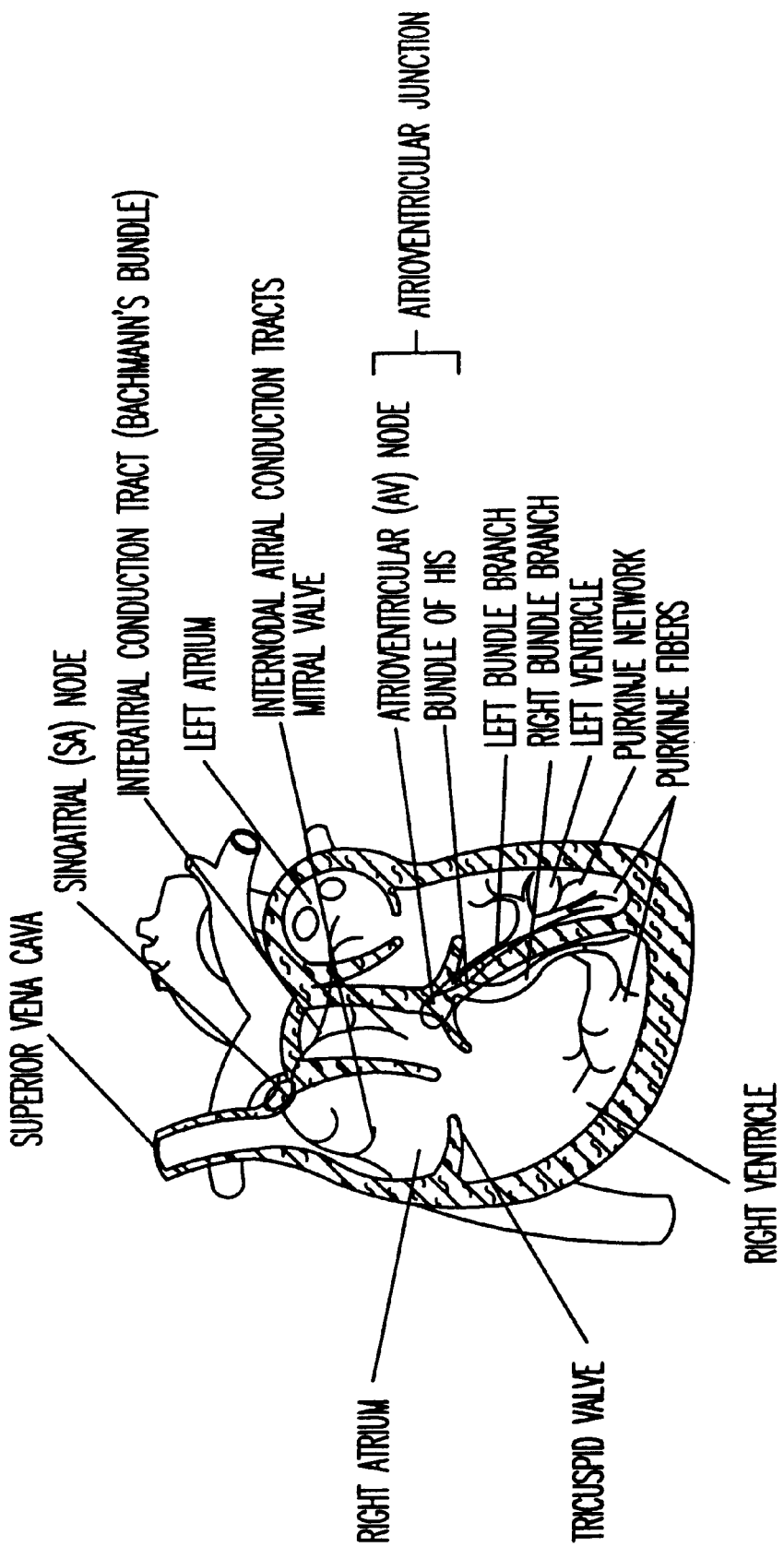
FIG. 1 is a schematic cut-away view of a human heart, in which the various relevant parts are labeled.
Figure 2:
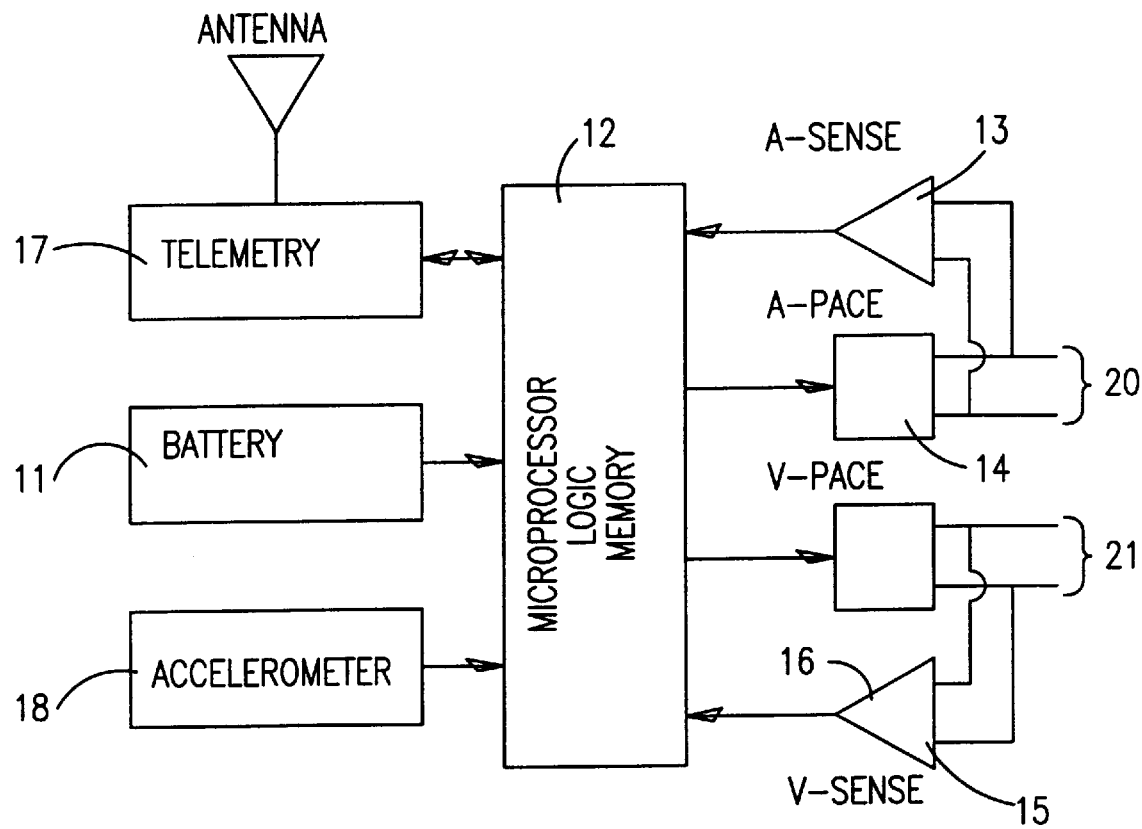
FIG. 2 is a schematic block diagram of a prior art dual-chamber pacer showing the functional blocks.
Figure 3:
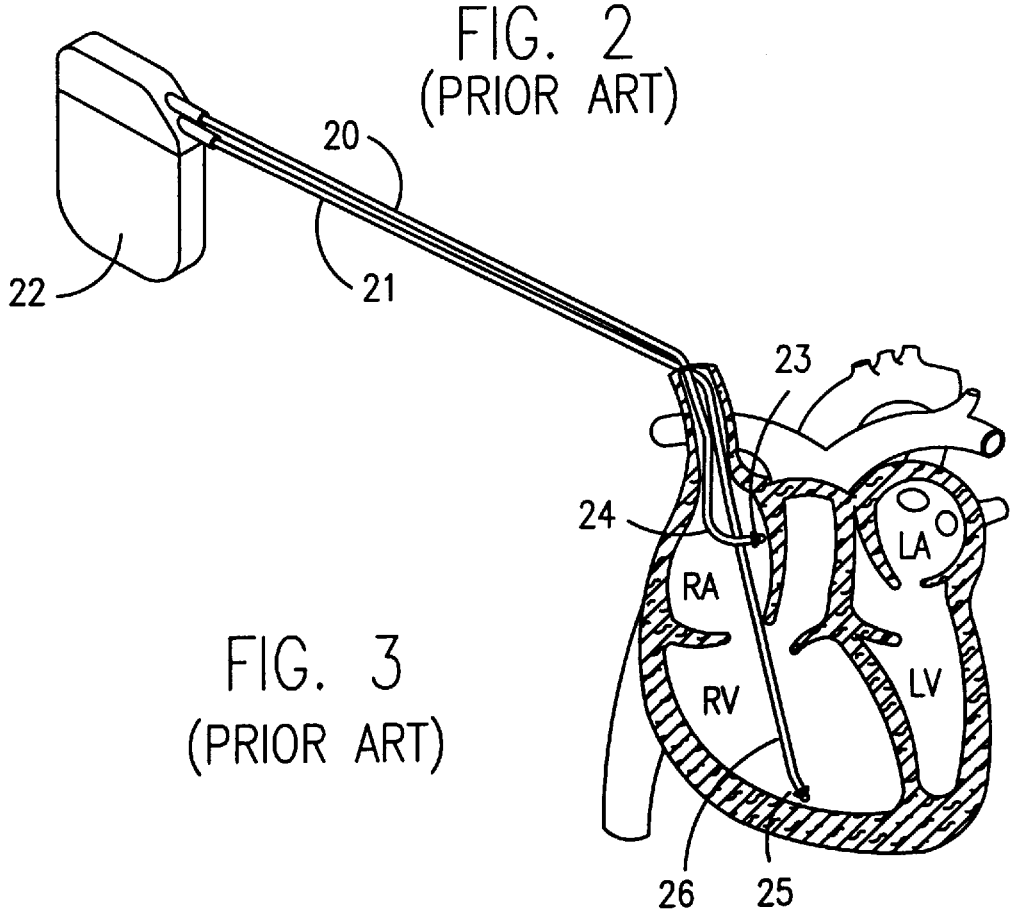
FIG. 3 is a schematic diagram of a prior art dual-chamber pacer showing conventional lead locations on right side of heart.
Figure 4:
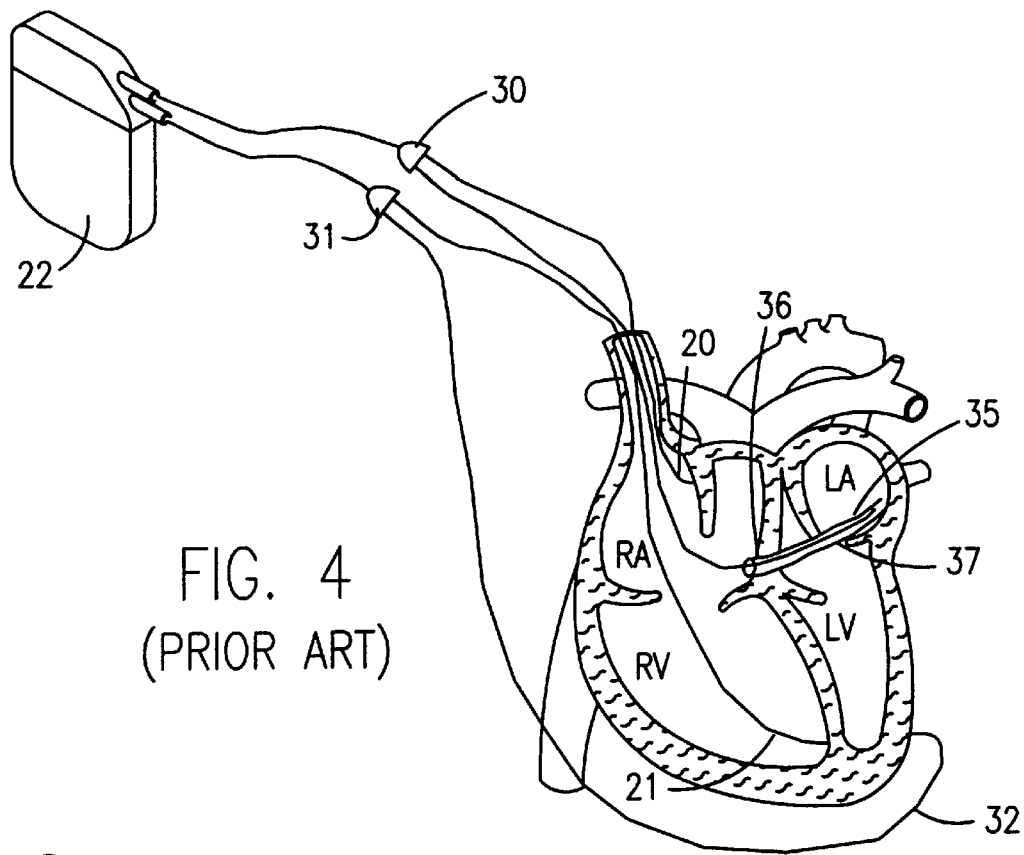
FIG. 4 is a schematic diagram of a prior art four-chamber pacer with an epicardial left ventricular lead.
Figure 5:
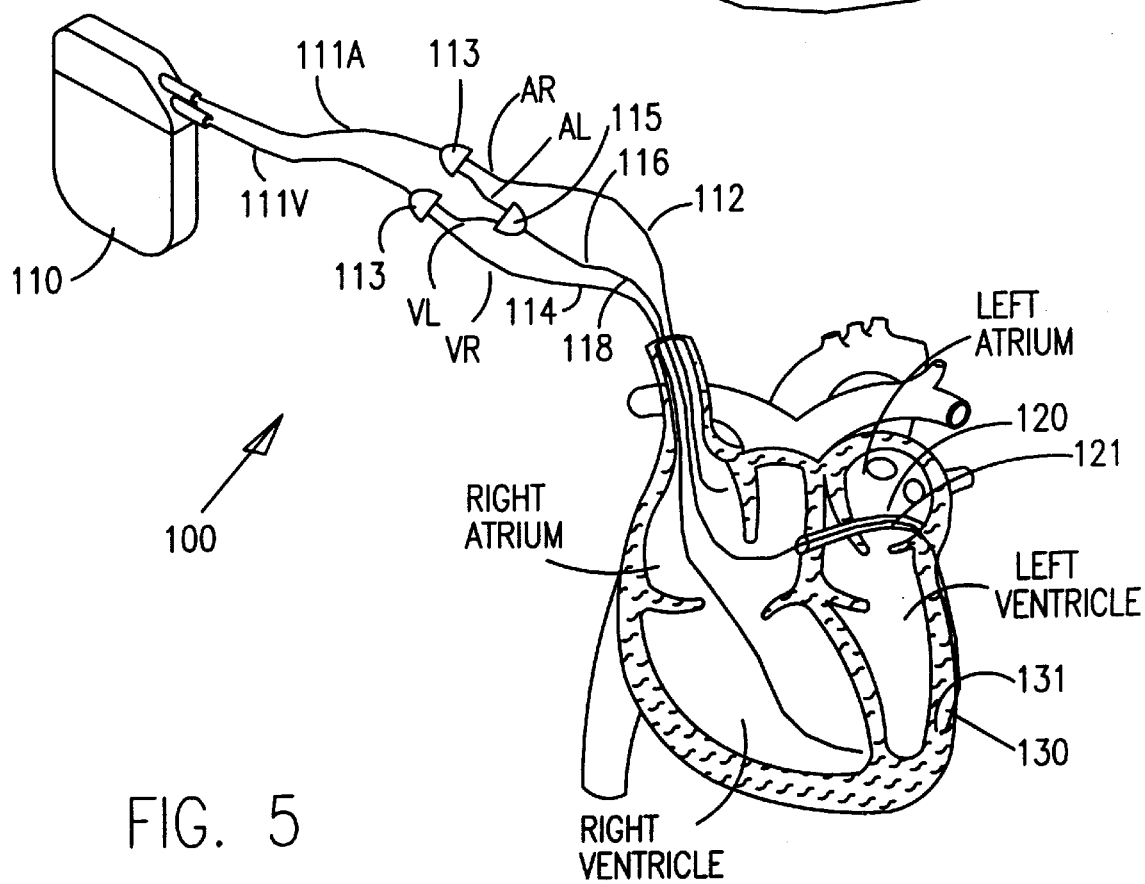
FIG. 5 is a schematic diagram of a four-chamber pacer according to the present invention implanted in a human body.

Referring now to FIG. 5, a four chamber pacing system 100 in accordance with one embodiment of the present invention comprises a pacer 110, from which two leads, 111A (atrial) and 111V (ventricular), extend. Leads 111A and 111B are each preferably comprise two conductors $A_L$, $A_R$ and $V_L$, $V_R$, respectively, and are each preferably connected to a standard bifurcated connector 113, which splits each pair of conductors. Conductors $V_R$, $A_R$, remain separate and form pacing leads 112, 114, while conductors $V_L$, $A_L$ are combined in connector 115 to form lead 116. Like lead 20 described above, lead 112 is anchored in and paces the right atrium. Similarly, lead 114 is anchored in and paces the right ventricle. Lead 116 enters the great cardiac vein through the ostium of the coronary sinus and paces both the left atrium and left ventricle as described in detail below.

Lead 116 consists of a proximal connector that makes electrical contact with pacer 110, a lead body 118 with a proximal set of electrodes 120 that lie in the coronary sinus (hereinafter "CS"), and a distal set of electrodes 130 that lie in the great cardiac vein (hereinafter "GCV") at the level of the left ventricle. While the present invention can be carried out in embodiments in which one or both of electrode groups 120, 130 comprise more than one electrode, as more fully described below, for simplicity's sake the following discussion is presented in terms of a single electrode 121, 131 respectively, at each of the two locations, CS and GCV.

The spacing between the CS and the GCV electrodes depends on the age of the patient and various anatomical details, such as are known in the art. The expected spacing is in the range of 6 to 30 cm, and most likely at least about 20 cm. It is preferred that the spacing between the electrodes in each group and the interconnections between electrodes within a group be selected to optimize the ratio between the desired signal and rejection of unwanted signals. In cases where there is more than one electrode at a location, the expected spacing range for electrodes within a group is between about 1 mm and about 30 mm.

Because the left atrium lies above the CS, the present invention provides a mechanism for supporting the atrial electrode 121 in good contact with the upper inside surface of the CS. At the same time, it is desirable to minimize deviation of the CS electrode from the coaxial lumen, since a stylet comprising a small diameter, relatively stiff, springy wire is temporarily inserted down the inside of the lead during the implant procedure so as to aid with lead placement. Small radius bends in the lead increase the likelihood of the stylet snagging the inside of the lead.

Figure 6:
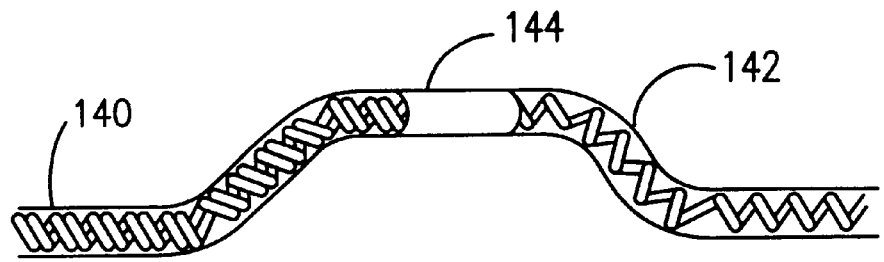
FIG. 6 shows a device for pacing or sensing the left atrium in accordance with one embodiment of the present invention.

The present invention solves these problems by providing a novel lead having a permanent set or deviation in it. The permanent set can be accomplished during manufacture, such that the set is accomplished by forming the lead with a permanently deviated sheath. A lead manufactured in this manner is shown in FIG. 6, wherein a bifilar lead 140 having a deviated sheath 142 includes a ring electrode 144 at its point of maximum deviation. Beyond ring electrode 144, lead 140 comprises a single wire.

Figure 7:
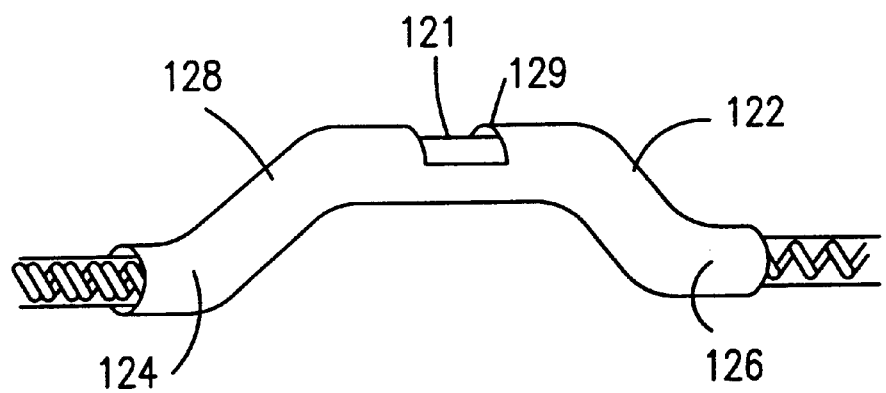
FIG. 7 shows a device for pacing or sensing the left atrium in accordance with a second embodiment of the present invention.

More preferably, however, the set or deviation of lead 116 is accomplished by passing a conventional flexible lead through a deviated collar 122, such as is shown in FIG. 7. Collar 122 is preferably tubular and comprises end portions 124, 126 and an arcuate, eccentrically shifted portion 128 therebetween. Collar 122 is preferably more rigid than lead 116 and is preferably formed such that end portions 124 and 126 are coaxial and are adapted to accommodate the diameter of lead 116. Eccentrically shifted portion 128 preferably includes a window or cut-out 129 on the side away from the axis of end portions.

When collar 122 is placed over the proximal electrode 121, lead 116 is forced to take on the deviated configuration of collar 122. When window 129 is aligned with electrode 121, electrode 121 is exposed to the inside wall of the CS. Because of the deviation, electrode 121 is held in contact with the wall of the CS and is thus able to provide pacing stimuli thereto. Thus, according to the present invention, lead 116 equipped with collar 122 is placed in the CS and oriented such that the deviated portion 128 and window 129 face toward the atrium. By directing the electrical signal in this manner, cross-signaling to the left ventricle is minimized.

Figure 8:
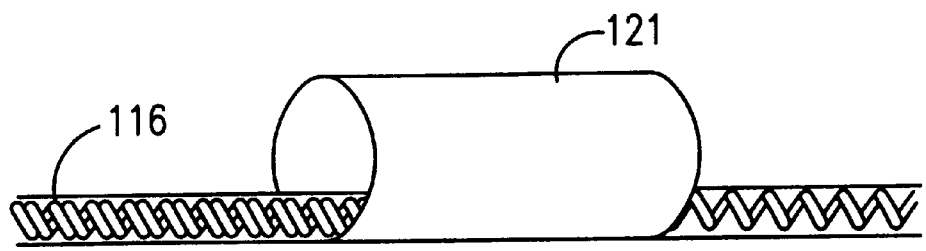
FIG. 8 shows a device for pacing or sensing the left atrium in accordance with a third embodiment of the present invention.

Referring now to FIG. 8, in an alternative embodiment, electrode 121 is formed so that it has a larger diameter than lead 116 and is eccentrically mounted such that it is not coaxial with lead 116. During implantation, the lead body is rotated so that the portion of the eccentric electrode furthest from the lead center points toward the left atrium.

Figure 9:
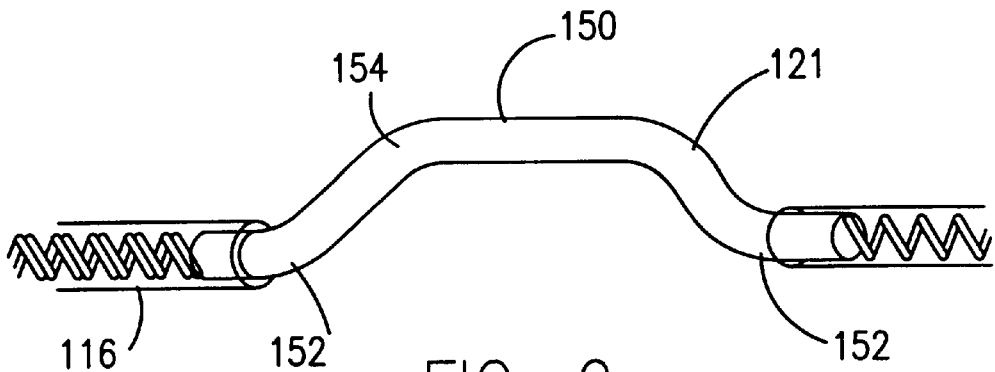
FIG. 9 shows a device for pacing or sensing the left atrium in accordance with a fourth embodiment of the present invention.

Referring now to FIG. 9, in still another embodiment, electrode 121 comprises a ring electrode 150 formed such that it is curved, with its two ends 152 being coaxial with lead 116 and its middle portion 154 forming a deviated portion that is not coaxial with lead 116. As described above, lead 116 can be rotated so that electrode 140 is placed in an optimal position for pacing the left atrium, wherein middle portion 154 is oriented toward the left atrium and contacts the upper inside wall of the CS.

In each of the foregoing embodiments, the diameter and extent of lateral offset of the CS-pacing portion of lead 116 are preferably such that they do not interfere with blood flow or normal operation of the heart.

Figure 10:
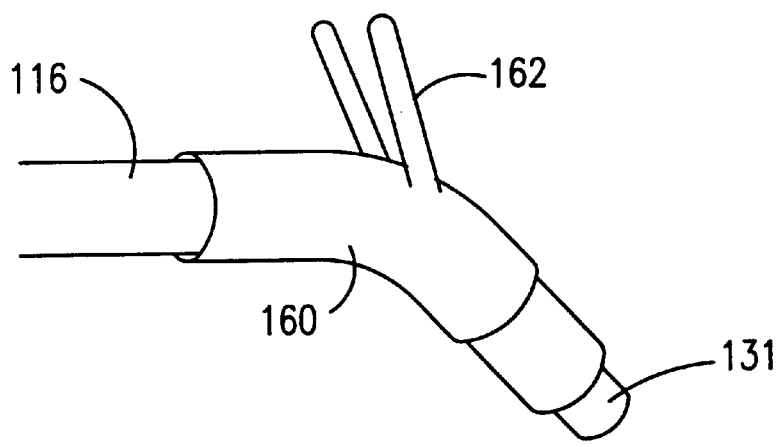
FIG. 10 shows a device for pacing or sensing the left ventricle in accordance with one embodiment of the present invention.

In order to simultaneously accomplish isolated pacing of the left ventricle using the same lead 116, the present invention further includes a bent tip and a means for anchoring the tip in the GCV. Alternatively, as shown in FIG. 10, a preferred embodiment for the distal end of lead 116 includes a sleeve 160 that slides over the end of lead 116 and causes it to assume a slightly bent configuration. Sleeve 160 preferably includes at least one, and more preferably two, tines 162 extending away from the axis of sleeve 160 and backward away from the distal end of the lead. The bent sleeve in combination with the tines 162 serves to anchor the distal electrode group 130 in the GCV. Preferably, lead 116 is oriented such that the signal transmitted to the left ventricle is maximized. Once positioned in this manner, the distal electrode group is held in place by tines 162 and is unlikely to shift.

Successful pacing of the left atrium and left ventricle independently of each other depends on optimal positioning of each electrode. Once the electrode in the CS is positioned for optimal atrial sensing and pacing, however, any subsequent rotation of the lead for the purpose of orienting the electrode in the GCV is likely to cause the CS electrode to shift away from its optimal position. In order to allow the GCV electrode 131 to be oriented and positioned independently of the CS electrode 121, a preferred embodiment of the present invention includes a slot or key in tip 131 (FIG. 10). One solution for this, considering that the terminal section from the CS ring to the tip will be silicone, is to use a stylet with a flattened end that fits into a slot in the pacing tip. Rotating the stylet relative to the lead body will cause the pacing tip to rotate in the GCV. This process can be performed until good sensing and pacing thresholds are achieved.

Figure 11:
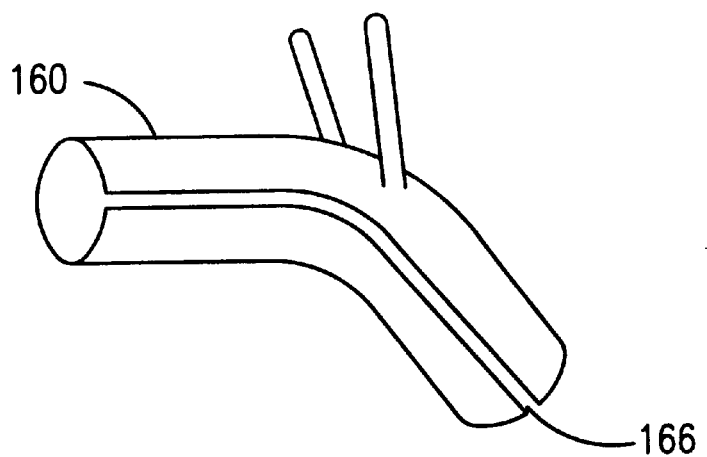
FIG. 11 shows a device for pacing or sensing the left ventricle in accordance with a second embodiment of the present invention.

For each electrode or group of electrodes, optimal orientation can be achieved by measuring the strength of the signal between electrode and a "dummy can" at the pacemaker pocket site, or from electrode to electrode for bipolar electrode configurations, and rotating the electrode, via lead or stylet, until the optimal signal strength is obtained. Instead of this method, or in addition to it, one or both electrode groups, or one or both of collar 122 and sleeve 160 can be provided with a radiopaque mark 166 (FIG. 11), so that the orientation of the component in question can easily be determined by conventional fluoroscopic-imaging techniques.

Generally the more conductors there are in a lead, the more likely there is to be a conductor failure. Therefore, it is desirable to minimize the number of conductors in a lead. A "brute force" four concentric conductor system would be very bulky and difficult to manufacture. Newer coated conductor multifilar leads appear to have potential advantages and keep lead diameter down to an acceptable level.

Using advanced lead technology, the present design can be extended to either bipolar at one site/unipolar at the other or full bipolar/bipolar. Modifications to the silastic sleeves similar to those described above are preferably made so as to accommodate the extra electrodes. One critical parameter is electrode spacing. Traditional bipolar leads have spacings of about 27 mm (ventricular) and 17 mm (atrial). Recent studies suggest that between 5 and 10 mm would offer a better trade off between signal amplitudes and signal-noise (i.e. interference rejection) ratio.

The electrodes used in the present invention may be constructed of any suitable electrode material, but preferably include a microporous coating such as the Irox process described in U.S. Pat. Nos. 4,679,572 and 4,762,136.

While sleeve 160 and collar 122 are shown as being tubular members that slide over the lead to the desired point of support, it will be understood that other configurations are possible. For example, collar 122 could comprise a non-tubular arcuate support, having clips or similar means for maintaining it in supporting engagement with the flexible lead. As mentioned above, either or both of the electrode groups 120, 130 can comprise one or more electrodes. As is known in the art of sensing and pacing leads, sensing can be from an electrode to the can of the pacer, from electrode to electrode within an electrode group, or from an electrode or electrodes within a first group to an electrode or electrodes in a second group. These sensed signals can be used internally by the implanted device and/or telemetered to a programmer or receiver for further analysis, processing and display.

Each electrode requires a conductor electrically connected to the sensing and pacing circuitry, so that a bipolar pacing device requires separate conductors for the anode and cathode. Hence, as more electrodes are added to the device, more conductors must be provided in the lead body. Conventional concentric lead configurations tend to become bulky when three, four or even more conductors are used, in part because of the concentric layers of insulation that must be present between adjacent coiled conductors. The bulk of such a conductor is particularly disadvantageous in the present situation, where the lead is placed in a relatively small vessel, namely the CS and GCV. Hence, it is preferred to use for lead 116 a multifilar lead in which the conductors are coiled not concentrically, but in parallel, such as is described in *PACE,* Vol. 15, November, Part II 1992: 1986–1990. This is particularly the case when one or more of the CS and GCV pacer/sensors includes more than one electrode.

Three different configurations of the present invention are described for illustrative purposes, with the understanding that these examples are selected from a range of configurations that are considered to be within the scope of the present invention. In a first embodiment, both the CS device and the GCV device are unipolar, with sensing and pacing occurring in a circuit that includes the pacer can. In a second embodiment the CS device is bipolar, while the GCV device is unipolar. In a third embodiment, both the CS and the GCV devices are bipolar.

In devices in which one or both of the CS and GCV pacers are bipolar or multipolar, if a sleeve or collar is used to facilitate contact with the vessel wall, that sleeve or collar can include a single large window that exposes all electrodes of that pacer. Alternatively, the sleeve or collar can be provided with a separate window for each electrode.

It will be understood that, while the present lead has been described in the context of certain indications and with certain objectives, it is equally advantageous in various other contexts. For example, the lead can be used in conjunction with a lead in the right ventricle to treat patients with bundle branch block, the lead can be used in conjunction with a lead in the right atrium to treat patients with interatrial conduction delay or block, or the lead can be used in conjunction with either two leads, one in the right atrium and one in the right ventricle, or with a single-pass RA/RV lead to synchronize both atria and both ventricles.

While preferred embodiments of the present invention are set out above, it will be understood that variations may be made to the present method without departing from the scope of the invention.

What is claimed is:

1. An apparatus for pacing four chambers of a heart, comprising:
    a power source housed in an implantable can;
    first, second and third leads having proximal and distal ends, each of said leads being electrically connected to said power source at its proximal end and adapted to extend from said can into a vein proximal the heart;
    said first lead connecting at its distal end to an electrode for electrical contact with the inside of the right atrium of the heart;
    said second lead connecting at its distal end to an electrode that for electrical contact with the inside of the right ventricle of the heart;
    said third lead connecting at a point proximal to its distal end to a CS electrode for stimulating the left atrium of the heart and said third lead connecting at its distal end to a GCV electrode for electrical contact with the inside of the great cardiac vein to stimulate the left ventricle of the heart, and having a collar, positioned adjacent said proximal point, which is more rigid than said third lead and which surrounds a portion of said third lead and which includes a window that allows said CS electrode to contact the inside of the coronary sinus.

2. The four-chamber pacing apparatus according to claim 1 wherein said third lead comprises at least two conductors.

3. The four-chamber pacing apparatus according to claim 2 wherein a first one of said conductors is electrically connected to said CS electrode and a second one of said conductors is electrically connected to said GCV electrode.

4. The four-chamber pacing apparatus according to claim 1 wherein said CS electrode includes a length of conductor having substantially coaxial ends and a deviated middle section therebetween, said deviated middle section being not coaxial with said coaxial ends.

5. The four-chamber pacing apparatus according to claim 1 wherein said GCV electrode includes an arcuate section adjacent said distal end.

6. The four-chamber pacing apparatus according to claim 1 wherein said third lead includes a removable sleeve that is more rigid than said third lead, said sleeve being positioned adjacent said distal end.

7. The four-chamber pacing apparatus according to claim 6 wherein said sleeve has a distal end and a proximal end and a length between said ends and is curved along said length.

8. The four-chamber pacing apparatus according to claim 7 wherein said sleeve has at least one tine.

9. The four-chamber pacing apparatus according to claim 6 wherein said sleeve surrounds a portion of said third lead and includes a window that allows said GCV electrode to contact said GCV wall.

10. The four-chamber pacing apparatus according to claim 1 wherein said third lead further includes a third electrode that in combination with said CS electrode forms a bipolar pacing device.

11. The four-chamber pacing apparatus according to claim 1 wherein said third lead further includes a third electrode that in combination with said GCV electrode forms a bipolar pacing device.

12. The four-chamber pacing apparatus according to claim 11 wherein said third lead further includes a fourth electrode that in combination with said CS electrode forms a bipolar pacing device.

13. An apparatus for pacing four chambers of a heart, comprising:
    a power source housed in an implantable can;
    first, second and third leads having proximal and distal ends, each of said leads being electrically connected to said power source at its proximal end for extending from said can into a vein proximal the heart;
    said first lead connecting at its distal end to an electrode for making electrical contact with the inside of the right atrium of the heart;
    said second lead connecting at its distal end to an electrode for making electrical contact with the inside of the right ventricle of the heart;
    said third lead connecting at a point proximal its distal end to a CS electrode for making electrical contact with the inside of the coronary sinus to stimulate the left atrium of the heart and connecting at its distal end to a GCV electrode for making electrical contact with the inside of the great cardiac vein to stimulate the left ventricle of the heart;
    said CS electrode including a ring electrode having substantially coaxial ends and a deviated middle portion therebetween;
    said deviated middle portion being not coaxial with said coaxial ends.

14. The four-chamber pacing apparatus according to claim 13 wherein said third lead comprises at least two conductors.

15. An apparatus for pacing four chambers of a heart, comprising:
    a power source housed in an implantable can;
    first, second and third leads having proximal and distal ends, each of said leads being electrically connected to said power source at its proximal end;

said first lead connecting at its distal end to an electrode for electrical contact with the inside of the right atrium of the heart;

said second lead connecting at its distal end to an electrode for electrical contact with the inside of the right ventricle of the heart;

said third lead connecting at a point proximal its distal end to a CS electrode for electrical contact with the inside of the coronary sinus to stimulate the left atrium of the heart and connecting at its distal end to a GCV electrode for electrical contact with the inside of the great cardiac vein and oriented so as to stimulate the left ventricle of the heart;

said third lead being flexible and including a collar that is more rigid than said third lead, said collar being positioned adjacent said proximal point and surrounding a portion of said third lead and including a window that allows said CS electrode to contact said CS wall, said third lead further including a sleeve that is more rigid than said third lead, said sleeve being positioned adjacent said distal point.

16. The four-chamber pacing apparatus according to claim 15 wherein said sleeve surrounds a portion of said third lead and includes a window that allows said GCV electrode to contact said GCV wall.

* * * * *

UNITED STATES PATENT AND TRADEMARK OFFICE
CERTIFICATE OF CORRECTION

PATENT NO.: 6,096,064

DATED: Aug. 1, 2000

INVENTOR(S): Routh

It is certified that errors appear in the above-identified patent and that said Patent is hereby corrected as shown below:

In column 6, line 12, delete "111B" and insert --111V--, therefor.

Signed and Sealed this

Tenth Day of April, 2001

Attest:

NICHOLAS P. GODICI

Attesting Officer

Acting Director of the United States Patent and Trademark Office